(12) United States Patent
Shampine

(10) Patent No.: US 9,733,192 B2
(45) Date of Patent: Aug. 15, 2017

(54) SLOT FLOW CELL

(71) Applicant: SCHLUMBERGER TECHNOLOGY CORPORATION, Sugar Land, TX (US)

(72) Inventor: Rod Shampine, Houston, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 14/962,049

(22) Filed: Dec. 8, 2015

(65) Prior Publication Data
US 2016/0178529 A1 Jun. 23, 2016

Related U.S. Application Data

(60) Provisional application No. 62/093,849, filed on Dec. 18, 2014.

(51) Int. Cl.
| | | |
|---|---|---|
| *G01N 1/10* | (2006.01) | |
| *G01N 21/85* | (2006.01) | |
| *G01N 21/01* | (2006.01) | |
| *G01N 21/05* | (2006.01) | |
| *G01N 11/02* | (2006.01) | |

(52) U.S. Cl.
CPC ............ *G01N 21/85* (2013.01); *G01N 21/01* (2013.01); *G01N 21/05* (2013.01); *G01N 11/02* (2013.01); *G01N 2201/061* (2013.01)

(58) Field of Classification Search
CPC .... G01N 21/05; G01N 21/03; G01N 21/0303; G01N 30/74; G01N 21/031
See application file for complete search history.

(56) References Cited

U.S. PATENT DOCUMENTS 8,013,845 B2 * 9/2011 Ostergaard ............ G06F 3/0421
                                                            178/18.09
8,304,733 B2 * 11/2012 Alameh ................ G06F 3/0308
                                                            250/349

(Continued)

FOREIGN PATENT DOCUMENTS

| DE | 19811876 A1 | 9/1999 |
|---|---|---|
| RU | 2096780 C1 | 11/1997 |
| WO | 00/11432 | 3/2000 |

OTHER PUBLICATIONS

Search Report issued in Russian Patent Application No. 2015154106 dated Dec. 15, 2016; 2 pages.

*Primary Examiner* — Tarifur Chowdhury
*Assistant Examiner* — Md M Rahman
(74) *Attorney, Agent, or Firm* — Michael L. Flynn; Jody Lynn DeStefanis; Robin Nava

(57) ABSTRACT

Apparatus include a test cell body having a first exterior surface, a second exterior surface, a cavity extending between the first exterior surface and the second exterior surface, and a first textured wetted plate and a second textured wetted plate disposed within the cavity. A fluid flow gap is defined between the first textured wetted plate and the second textured wetted plate. An illuminator is disposed between the second textured wetted plate and the second exterior surface, and a viewing window formed within the first exterior surface. The first textured wetted plate and the second textured wetted plate may be transparent.

22 Claims, 7 Drawing Sheets

(56) References Cited

U.S. PATENT DOCUMENTS

| | | | |
|---|---|---|---|
| 8,441,467 B2 * | 5/2013 | Han | G06F 3/04883 178/18.09 |
| 2008/0284925 A1 * | 11/2008 | Han | G06F 3/0425 349/12 |
| 2009/0169428 A1 | 7/2009 | Gillespie et al. | |

* cited by examiner

SLOT FLOW CELL

RELATED APPLICATION INFORMATION

This Patent Document claims priority under 35 U.S.C. § 120 to U.S. Provisional Patent Application No. 62/093,849 filed Dec. 18, 2014, which is incorporated herein in its entirety.

FIELD

The present disclosure is related in general to materials and techniques useful in treating subterranean formations, and in particular, instrumental methods and apparatus useful for simulating the flow of treatment fluids through a fracture formed in a subterranean formation.

BACKGROUND

This section provides background information to facilitate a better understanding of the various aspects of the disclosure. It should be understood that the statements in this section of this document are to be read in this light, and not as admissions of prior art.

In the technical field of hydraulic fracturing, one major challenge impeding an understanding of the detailed mechanics of fracturing, proppant flow, and closure behavior is an inability to actually view the process. Rock, most often being at least opaque, obscures any view of what is occurring therein, and typically, the subterranean formation operation occurs 5,000 to 20,000 feet away from the surface. Further, in some cases, important cause and effect events take place tens to hundreds of feet away from the wellbore deeper into the subterranean formation region into which the fracture extends.

Many approaches to better understand the detailed effects of fracturing processes have been attempted over the years. One approach includes a methodology referred to as 'mine back'. In a mine back operation, colored sand is placed in a fracture formed near an existing mine in a subterranean formation. Once the hydraulic fluid pressure is decreased and the fracture has closed upon the sand, the mine is further extended toward the fracture in layers. The sand deposits are recorded with photos as they are revealed. Such an approach is known to be expensive and time consuming, as well as limited to very special situations and formations.

Some other approaches have included use of microseismic and tilt meter measurements to ascertain some degree of understanding of the extent and dimensions of downhole fractures in real wells. Also, radioactive sand has been used to comprehend near well bore sand distributions, to some limited degree. In another approach, chemical tracers pumped in with the fracturing fluid were used provide some indication of fracture length due to the time that elapsed for the tracer to flow back to flow back.

On a large laboratory scale, blocks of rock and ice that have been fractured at scales of up to 1 meter on a side have been used. The fractures are made in the blocks at significant hydrostatic and confining pressures in order to ascertain the mechanisms that may be involved in fracturing. Also, slot flow cells have been used to visualize simulated behavior of fracturing fluids as they are pumped into the cells. These cells typically consist of two parallel transparent plates of acrylic or polycarbonate with a spacer between to define a gap. Often, structural members constrain the edges and in some cases, may run across the face of the cell. Also, these cells all suffer from significant wall deflections, as well as have substantially smooth walls. In some cases, cells used about 1" thick acrylic plates for the viewing ports and also for the flow surface. This meant that a damaged flow surface necessitated replacing the pressure containment at a significant cost. Also, it was not economically feasible to have a very stiff cell, and the deflection of 1" acrylic over a 4' span was easily visible with only hydrostatic pressure due to water.

It remains an ongoing need to provide improved methods and apparatus for understanding of the detailed mechanics of formation fracturing, proppant flow, and fracture closure dynamics, such need met, at least in part, by embodiments disclosed in the following disclosure.

SUMMARY

This section provides a general summary of the disclosure, and is not a necessarily a comprehensive disclosure of its full scope or all of its features.

In aspects of the disclosure apparatus include a test cell body having a first exterior surface, a second exterior surface, a cavity extending between the first exterior surface and the second exterior surface, and a first textured wetted plate and second textured wetted plate disposed within the cavity. A fluid flow gap is defined between the first textured wetted plate and the second textured wetted plate. An illuminator is disposed between the second textured wetted plate and the second exterior surface, and a viewing window formed within the first exterior surface. The first textured wetted plate and the second textured wetted plate may be transparent. In some aspects, the first textured wetted plate and the second textured wetted plate have opposed mated surfaces, and may include textures such as simulated split rock, hexagonal textured surfaces, ripple textured surfaces, fine grain textured surfaces, and the like. In some aspects, the first textured wetted plate and the second textured wetted plate have multiple dimensional scale texture patterns, where the texture patterns are defined on a micrometer scale, a 1 mm to 5 mm scale, and a 10 mm to 200 mm scale.

The first exterior surface may include a deflection brace disposed within the viewing window and adjacent the first textured wetted plate. Also, a plurality of spacers may be placed between the first textured wetted plate and the second textured wetted plate, and adjacent the fluid flow gap to define a fluid flow gap width. In some aspects, the fluid flow gap has an adjustable width. The adjustable width may varied by deflection of the first textured wetted plate under pressure, by sliding the first textured wetted plate and the second textured wetted plate relative one another, where the plates have steps formed in opposing surfaces, or any other suitable means. In some cases, a portion of the fluid flow gap includes a porous plate disposed therein.

In some other embodiments of the disclosure, systems include a test cell having a fluid flow gap defined between a first textured wetted plate and the second textured wetted plate, where the plates are transparent. An illuminator is disposed adjacent the second textured wetted plate, and a viewing window positioned adjacent the first textured wetted plate. A test fluid is disposed within the fluid flow gap, and in some cases, the test fluid is a subterranean formation treatment fluid, which may or may not include proppant entrained therein.

Another embodiment according to the disclosure is a system having a test cell fluid flow gap defined between a first textured wetted plate and a second textured wetted plate, where the plates are transparent. A plurality of spacers are disposed between the first textured wetted plate and the second textured wetted plate, and adjacent the fluid flow gap to define a fluid flow gap width. A viewing window is positioned adjacent the first textured wetted plate. In some cases the first textured wetted plate and the second textured wetted plate are opposed mated surfaces having a pattern selected from one of simulated split rock, hexagonal texture, ripple texture, and fine grain texture.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

Figure 1:
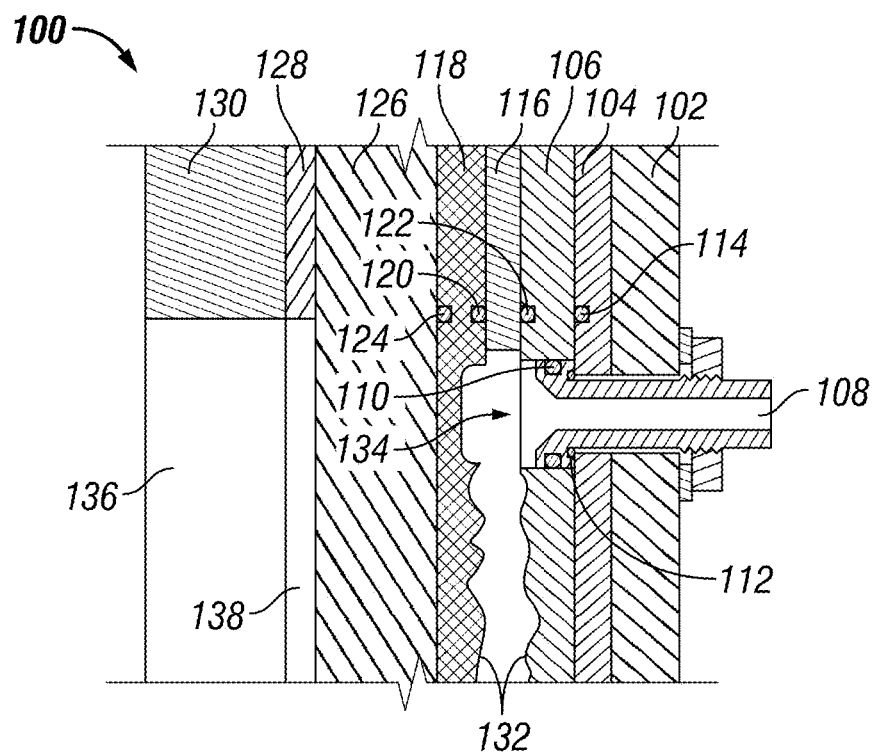
FIG. 1 illustrates in cross-sectional view, an embodiment of a test cell according to the disclosure.

The following description of the variations is merely illustrative in nature and is in no way intended to limit the scope of the disclosure, its application, or uses. The description and examples are presented herein solely for the purpose of illustrating the various embodiments and should not be construed as a limitation to the scope and applicability of such. Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of concepts according to the disclosure. This description should be read to include one or at least one and the singular also includes the plural unless otherwise stated. The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited. Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

Embodiments according to the disclosure provide methods and/or apparatus for understanding of the detailed mechanics of formation fracturing, proppant flow, and fracture closure dynamics, on a laboratory scale, or otherwise separate from a subterranean formation, and without the use of subterranean formation core samples. Embodiments make use of such technologies as fiber optic sheets, electroluminescent panels, and/or doped acrylic back lights. In some aspects, doped acrylic panels were found useful in embodiments, as these panels were capable of withstanding thousands of pound per square inch compressive loads while delivering uniform light of select colors, and which are available in sheets of 4 foot by 8 foot in area. In some embodiments, doping is achieved by embedding transparent particles in an acrylic sheet, which creates an evenly illuminated panel, requiring no additional treatment such as surface etching, engraving or printing to achieve bright surface illumination. Nonlimiting examples of such panels are those provided under the trade name ACRYLITE® LED, available from Evonik Industries AG, Essen, Germany. A white reflective sheet is typically used behind the panel to reflect light forward, as the illuminated panel transmits light uniformly in both directions. When incorporated in the construction of a flow cell, these panels allow the back panel of the flow cell to be a steel wall of essentially any suitable stiffness required, while still allowing accessible visual inspection of flow patterns there through. One or more layers of light diffusing doped plastic may also be useful to further improve the uniformity of the light output and also to hide thermal conductive wires. Further, flow ports can easily be run through the back plate and illumination system without compromising the function thereof. Some embodiments may benefit from separating the pressure containment components from the components in contact with test fluids.

FIG. 1 illustrates in cross-sectional view, an embodiment of a test cell according to the disclosure. In a general layered construction as depicted, test cell 100 includes a back plate 102, which is an adequately stiff structural member, such as steel and the like, that supports the layered structure under high pressure loads used in simulating fluid activities such as formation fracturing, proppant flow, and fracture closure. The next layer is the illuminator 104 which may in some cases consist of many layers, such as a reflective sheet, a doped acrylic light pipe that is edge lit, a diffuser sheet, and a cover plate, as shown and described in further detail in FIG. 2. A first textured wetted plate 106 is disposed adjacent the illuminator 104, and may have a flow fitting 108 that is sealingly disposed into first textured wetted plate 106 with O-ring 110. Another O-ring 122 seals the flow fitting to illuminator 104. A vacuum clamping system may be used to secure the first textured wetted plate 106 to the illuminator 104 with a large O-ring seal 114 to retain vacuum. A spacer 116 is sealed to the first textured wetted plate 106 and the second textured wetted plate 118 with O-rings 120 and 122.

This allows the cell gap to be adjusted easily and reliably. A similar vacuum clamping system with O-ring 124 holds the second textured wetted plate 118 sealingly against the structural viewing plate 126. In some aspects of the disclosure, primarily transparent heating elements, such as, but not limited to, indium-tin oxide conductors, fine sized copper wires, or other conducting materials with good light transmission, may be disposed on the outside of the textured wetted plates to apply a target temperature as close to the flow area as possible, without significantly obscuring the view. Temperatures of up about 150 deg F., or even up to 200 deg F. are examples of suitable temperatures provided by the transparent heating elements.

The structural viewing plate 126 is selected from a material, which provides acceptable deflection under pressure inside the cell, and is not limited in selection by either cost or chemical compatibility or resistance. In some cases, structural viewing plate 126 is material based upon annealed acrylic, or in some other cases, annealed polycarbonate. A shim 128 may be imposed between the structural viewing plate 126 and the outer steel structure 130 to minimize the stress concentration in the more expensive components, such as the structural viewing plate and textured wetted plates. In some aspects, the structural viewing plate 126 may be designed according to one of many window designs according to the ASME Pressure Vessels for Human Occupancy code, PVHO-1-2012, which is included herein by reference thereto. In some other aspects, the structural viewing plate 126 may be designed according to underwater viewing window practice, which allows considerable flexibility in size and pressure rating.

In some aspects according to the disclosure, textured wetted plates 106 and 108 may have specific texture patterns machined into their surfaces 132, and may have flow distribution structures 134 also incorporated therein. In some cases, the textures machined into their surfaces 132 are arbitrary, or otherwise random, while in other cases, the textures may be a select pattern. Combinations of both general texture types may be useful as well. Flow ports leading out the side of the plates may also be incorporated easily as well. In some embodiments, the structural connection securing the back plate 102 and the outer structure 130 may be designed to allow the stack of layers to expand and contract without significant changes in the clamping load. In some aspects, large air cylinders or hydraulic cylinders, with an attached accumulator, may provide such a function, as well as allowing the cell to be heated and cooled without leakage of the test fluid. As further depicted in FIG. 1, outer structure 130 and shim 128 may include window 136 and 138 for allowing visual observation of intra-cell fluid activity occurring between textured wetted plates 106 and 108.

Figure 2:
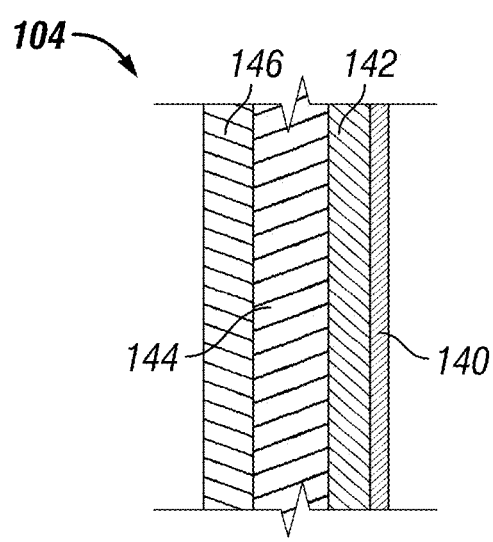
FIG. 2 depicts in cross-sectional view, illuminator useful in some embodiments according to the disclosure.

FIG. 2 depicts in cross-sectional view, illuminator 104. Illuminator 104 may include layers such as a reflective sheet 140, a doped acrylic light pipe 142 that is edge lit, a diffuser sheet 144, and a cover plate 146. Doped acrylic light pipe 142 may be any suitable device useful for transporting and/or distributing light energy from a light source to an area of illumination, as optical waveguide, made of transparent solids that contain the light by total internal reflection, such as those described above.

Figure 3:
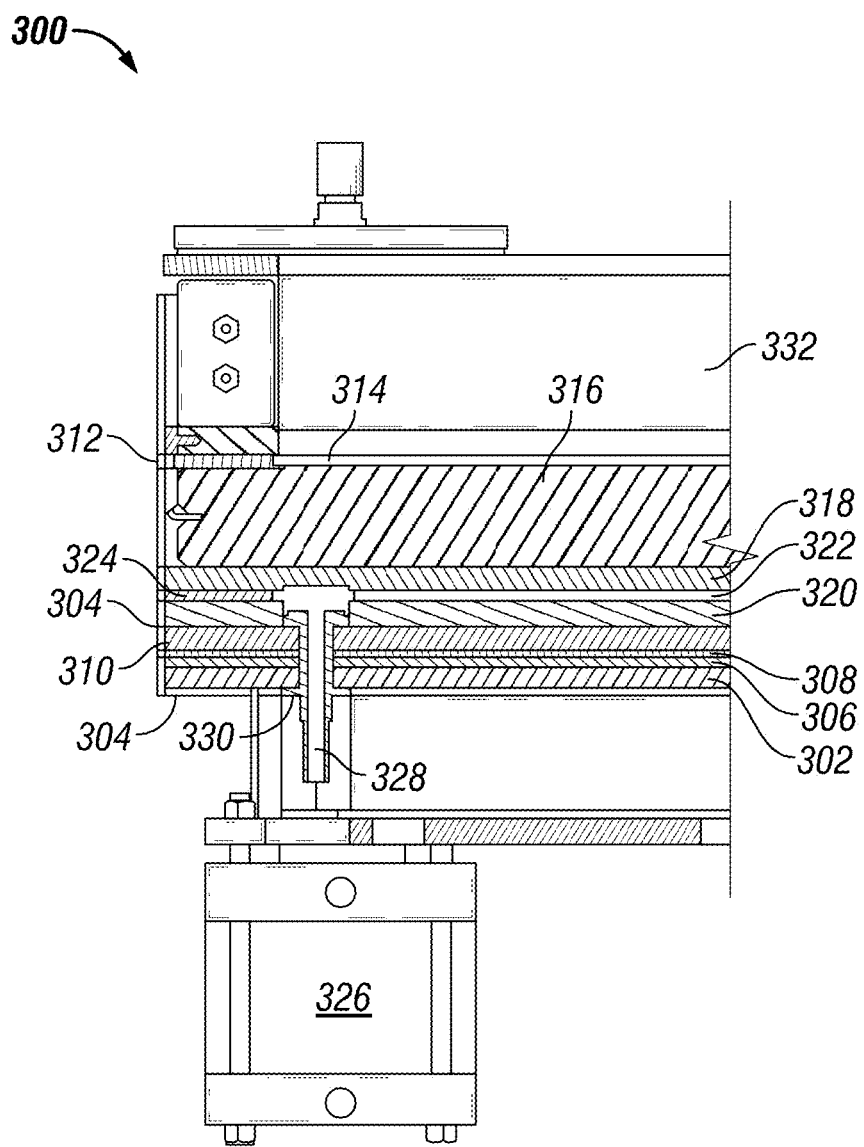
FIG. 3 shows a cross-sectional view of a test cell according to some embodiments of the disclosure.

Now referencing FIG. 3, which depicts another cross-sectional view of a test cell according to some embodiments of the disclosure. Test cell 300 includes a back plate 302 (approximately 1 inch in thickness) and outer steel structure 304, which secures and/or contains back plate 302 and other components. A light plate 306 (approximately 0.25 inch in thickness), such as a doped acrylic light pipe or other suitable optical waveguide, is disposed adjacent back plate 302. Diffusion plate 308 (approximately 0.18 inch in thickness) is positioned adjacent light plate 306, and cover plate 310 (approximately 1 inch in thickness) disposed adjacent diffusion plate 308. On the opposing side of the layered structure depicted is cover plate 312 (approximately 0.5 inch in thickness) having viewing window 314 formed therein, and viewplate 316 (approximately 4 inches in thickness) disposed adjacent cover plate 312. Viewplate 316 may be constructed of a material, which allows sufficient viewing of intra-cell fluid activity. First textured wetted plate 318 and second textured wetted plate 320 are disposed between viewplate 316 and cover plate 310, as depicted. First textured wetted plate 318 and second textured wetted plate 320 define fluid flow gap 322 there between, on one end of the illustration, and sealing plate 324 (approximately 0.1 inch in thickness) is disposed between first textured wetted plate 318 and second textured wetted plate 320 on the other end. Pump 326 may supply test fluid at target pressure and volume into fluid flow gap 322 via channel 328 contained with flow fitting 330. Test cell 300 is of a design which provides up to 20 psi of fluid pressure within fluid flow gap 322 and a viewing area 332 of approximately 3 foot by 7 foot.

Figure 4:
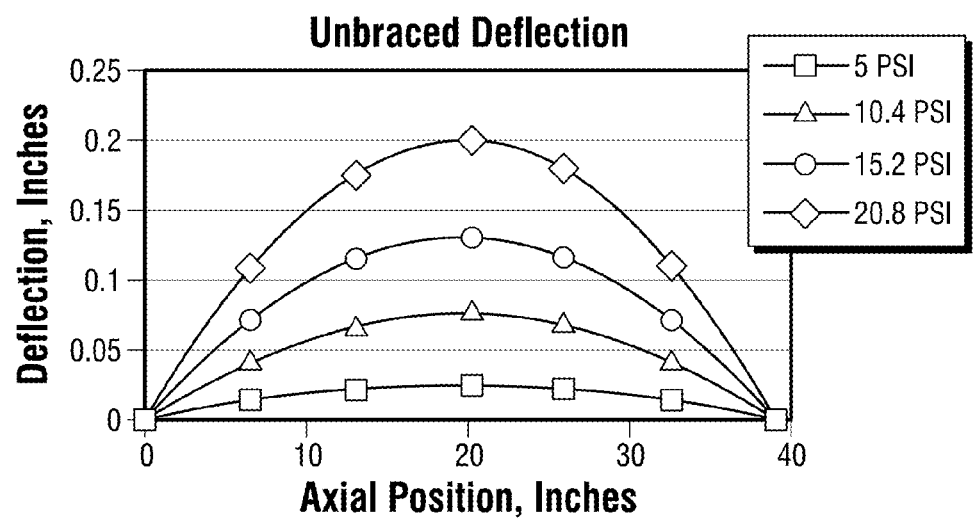
FIGS. 4 and 5 graphically depict the deflection across the center of view plate for some test cells embodiments according to the disclosure.
Figure 5:
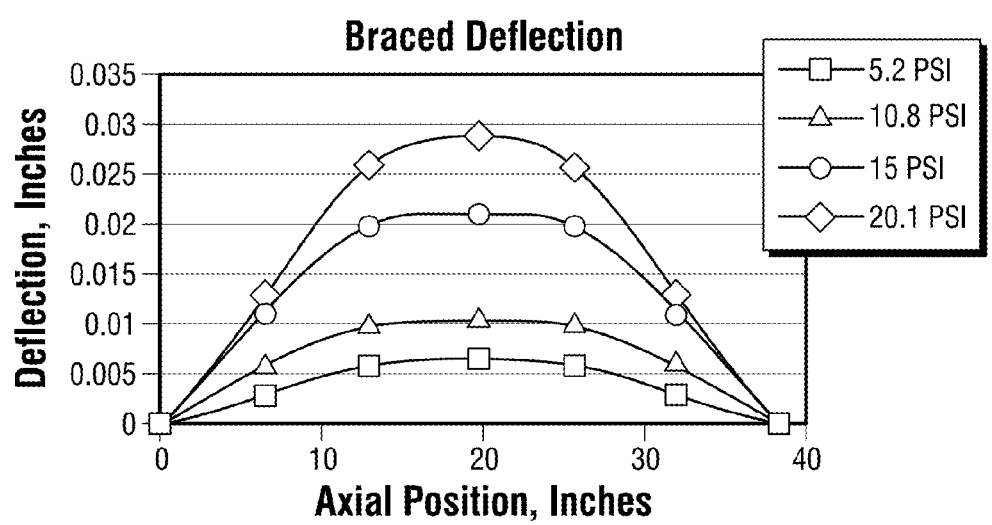

FIG. 4 graphically depicts the deflection across the center of the view plate for test cells 300, where viewing area 332 is unbraced, and has a width of about 40 inches. This deflection is small relative to a gap of 0.1 inches for low pressure of 5 psi, but rises to un-acceptable levels at high pressures, such as 10.4 and 20.8 psi. In some cases, for viscous test fluids, it may be necessary to pump the test fluid into the cell fluid flow gap 322 at the high end of the pressure rating, and then allow the pressure to bleed off to a lower pressure in a useable range, such as about 15 psi or less, or even 5 psi or below. FIG. 4 graphically depicts the deflection across the center of the view plate for test cells 300, where a viewing area 332 is braced by a support surface, and has a width of about 40 inches. With reference to FIG. 5, the deflection problem depicted in FIG. 4 is significantly reduced by sacrificing some of the view with a single brace, or support surface, integrated into outer steel structure 134 and disposed upon viewplate 316 across the shortest dimension of viewing area 332 of test cell 300. As shown in the graph of FIG. 5, the single center brace, or support surface, decreased the deflection will drop by a factor of approximately ten, as compared to an unbraced viewing area. As such, test fluids, including viscous test fluids, may be pumped into the test cell fluid flow gap 322 at the high end of the pressure rating with acceptable deflection of the viewing area.

Figure 6:
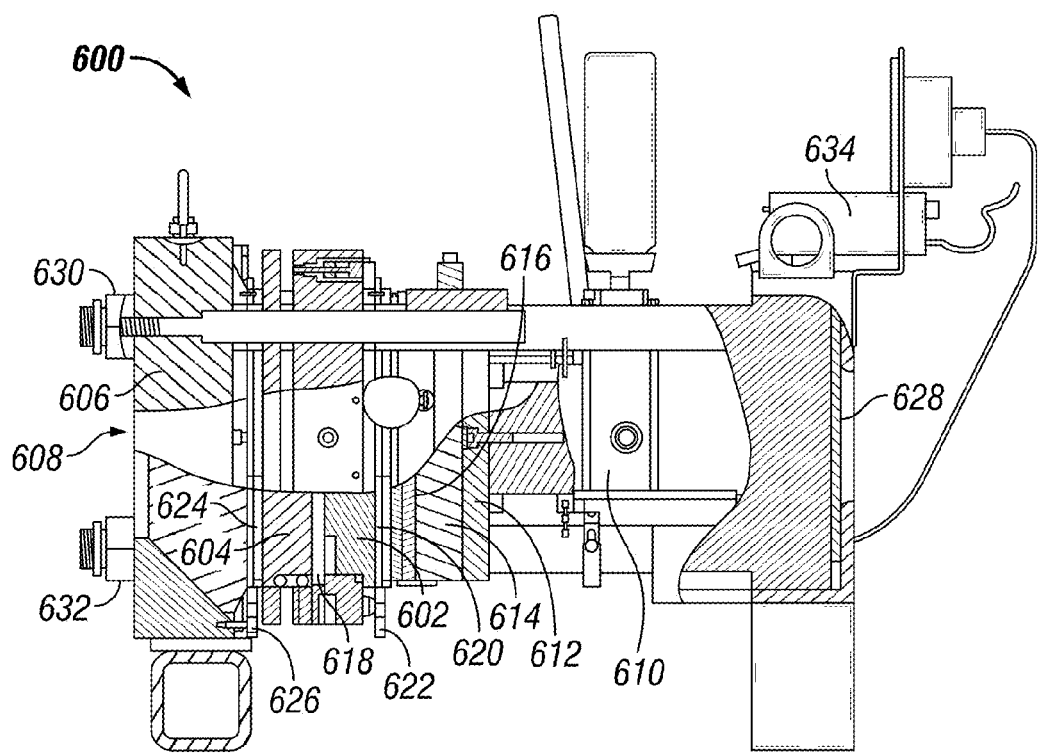
FIG. 6, illustrates in partial cut away cross-sectional view, another test cell embodiment in accordance with the disclosure.

With reference to FIG. 6, which illustrates in partial cut away cross-sectional view, another test cell embodiment in accordance with the disclosure, with very significant pressure capability in a 12-inch diameter test cell design. Test cell 600, which includes many similar features as described in the above embodiments, is of a design that can withstand up to 970 psi of fluid pressure and a clamping load of 50 tons. In the embodiment depicted, first textured wetted plate 602 can be moved toward the other second textured wetted plate 604 by up to 0.5 inches while under pressure and load. Textured wetted plates 602 and 604 are approximately 2 inches in thickness. This system uses a conical acrylic window provided viewplate 606 (approximately 4 inches in thickness) disposed on the side at 608. Such design elements provide significantly higher pressure capability than the flat window design depicted in FIGS. 1-3, while still only using about 4 inch thick acrylic viewplate 606. While in some cases, viewing windows requiring acrylic viewplate greater than about 4 inches in thickness are available, these may be extremely costly, as the slab forming such requires a custom slush cast. Viewplates of thickness of about 4 inches and below are more economical and readily available as they may be manufactured by cell casting.

Test cell 600 further includes cylinder 610 of sufficient pressure capacity for applying the load on first textured wetted plate 602, backing plate 612, illuminator 614 which may in some cases consist of many layers, such as a reflective sheet, a doped acrylic light pipe that is edge lit, a diffuser sheet, and a cover plate 616. Cell fluid flow gap 618 defined between first textured wetted plate 602 and second textured wetted plate 604 may have a width of approximately 0.5 inches when not under load applied by cylinder 610. First heat disc 620 may be disposed between illuminator cover plate 616 and first textured wetted plate 602, and secured in place with cradle 622, while second heat disc 624 may be disposed between viewplate 606 and second textured wetted plate 604, with cradle 626 securing second heat disc 624. Heat discs 620 and 624 are approximately 0.5 inches in thickness. Test cell 600 further includes a plate support 628 disposed on one end, which cooperates with nuts 630 and 632 to hold the components of the test cell in place when in operation and under load. A data recorder/control component 634 may be integrated as well.

Embodiments according to the disclosure relate to simulating the surface of actual rock face by fractures formed in a subterranean formation or fractures already existing in the formation. This is achieved by surface roughness or non-planar features superimposed on the fluid flow gap surfaces of textured wetted plates used in accordance with the disclosure. In one case, to mimic such rock faces, castings of the opposing surfaces of a split rock, which provided mated surfaces, were prepared, and vacuum formed acrylic plates were made from the casting forms. The vacuum formed plates were then sandblasted and replicated the split rock surface. Acrylic textured plates were also prepared using a 3D printing technique to provide steps and angles. These cells worked well because of the micro-scale roughness of the 3D printed surfaces. The 3D printing pattern included a stereolithography based on a mathematically defined synthetic rock texture.

For some embodiments described herein, a set of textured plates that were machined in large scale (i.e. 4 foot by 8 foot area plates) that provide a graduated set of textures across three length or dimensional scales were prepared. Such length scales included micrometer scale roughness, where the roughness characteristic dimensions are smaller than typical sand grains, and comparable to fiber diameters. A second medium scale roughness included features between sand grain size (about 100 to about 20 mesh) and typical fracture widths (about 2 to about 5 mm). A third large scale roughness feature was significantly larger than the fracture width but significantly smaller than the cell dimensions, and were about 10 to about 200 mm length. The sets of textured plates included smooth plates, sand blasted plates, ripple textured plates, hexagonal textured plates, and fine grain synthetic rock texture plates. It was found that sand blasted plates provided only a microscale roughness. The more complex plates provided textures with all three levels of roughness.

Figure 7:
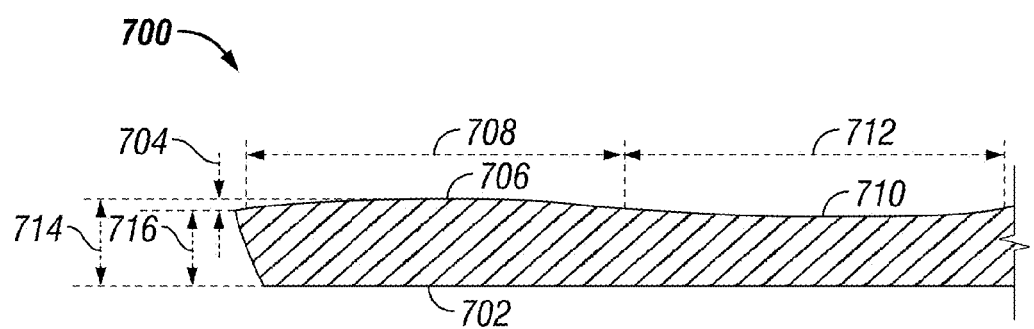
FIG. 7 depicts in cross-sectional view, a ripple textured wetted plate useful in some embodiments according to the disclosure.

The ripple texture plates represented the minimum level of texture complexity that produces reliable results. The ripple texture plates had a sine wave pattern with a period of about 8 inches, amplitude of about 0.2 inches, and were prepared by machining a blank smooth plate using a 0.25-inch diameter ball end mill and 0.125 inch center to center passes. This produced a rippled sine wave texture pattern with slightly pointed areas between the each of the mill passes. The plate was then sand blasted to yield a uniform microscale roughness. A cross-section view of the ripple plate is provided in FIG. 7. The ripple texture plate was prepared from a 4 foot by 8-foot sheet of transparent acrylic plexiglass. Side 702 was maintained smooth, and the opposing side was subject to the machining described above. The sine wave pattern had amplitude of about 0.2 inches (shown at 704) with a period of about 8 inches, defined by crest 706 with length of 4 inches (shown at 708), and trough 710 with length of 4 inches (shown at 712). The starting thickness was 2 inches (shown at 714), which was maintained for the peak of crest 706, and the thickness of the plate at the bottom of trough 710 was 1.8 inches (shown at 716).

Figure 8:
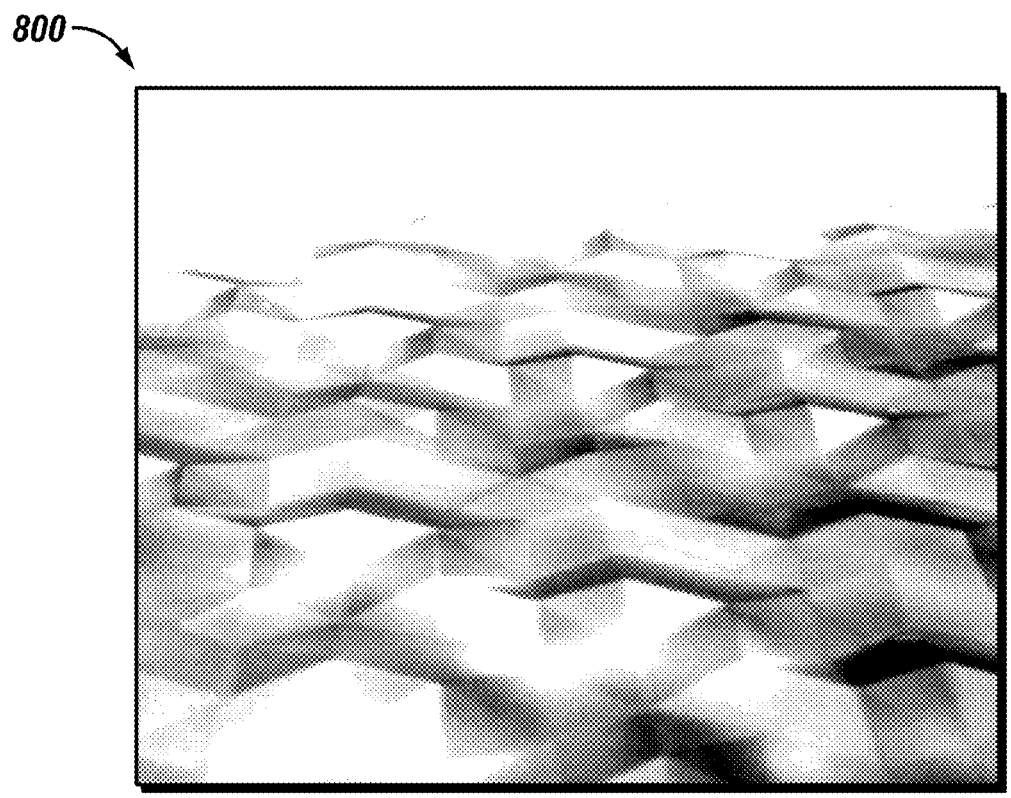
FIG. 8 shows a hexagonal textured plate surface in a perspective view in accordance with the disclosure.

Now referencing FIG. 8, which depicts a hexagonal textured plate surface in a perspective view. The hexagonal textured plate 800 was prepared using similar machining technique described above to generate the medium scale roughness, but the surface was based on a highly decimated synthetic rock texture with triangles between the specified points. This pattern functions in both horizontal and vertical positions, but the hexagonal axes introduce a visible defect in some experiments that the ripple texture did not provide. However, the ripple texture face works properly with the ripples in the horizontal direction.

Figure 9:
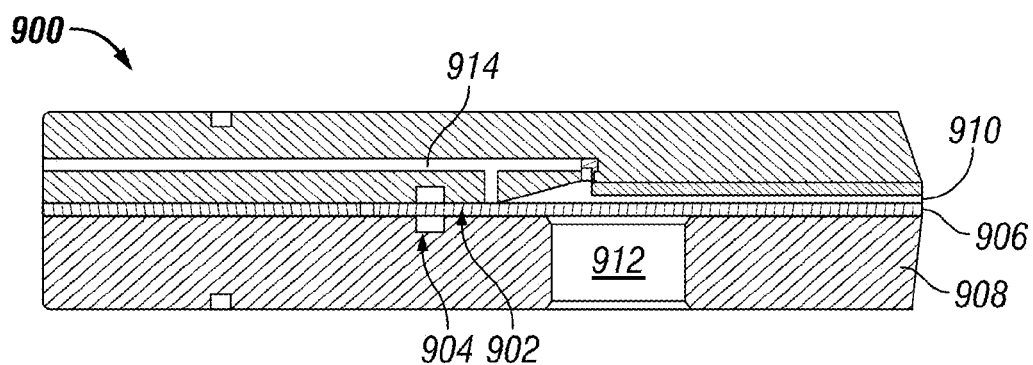
FIG. 9 illustrates in cross-sectional view, an embodiment of a variable width test cell fluid flow gap according to the disclosure.

In some embodiments according to the disclosure, the textured plate system is one where the test cell fluid flow gap can be varied, which allows the test fluid to actually open the gap, thus simulating a fracture. This gap can also be closed upon proppant placed therein, to study motion and activity during closure. With reference to FIG. 9, which depicts such an arrangement in a cross-sectional view, the test cell 900 includes a moving plate 902 with seals 904 disposed on both sides. One side 906 of this plate 902 is in contact with the texture plate 908. The other side has a cavity 910 above it filled with fluid. By controlling the fluid pressure the moving plate may be allowed to flex away from the texture plate, or be pressed against it. Inserting shims into the cavity may control the cavity depth, and resulting fracture width. The large vertical hole 912 in this illustration is the slurry inlet. The small horizontal hole 914 is the fluid passage to the cavity. Different thicknesses and materials of the moving plates may be used to simulate different rocks. Thick plates may require a relief groove around the moving area, on the fluid control side, to provide sufficient ability to move. This embodiment allows a simulated fracture to be opened, by pumping against a constant pressure above moving plate 902, followed by filling with proppant. After this, fracture closure may be simulated by slowly bleeding down the fluid pressure on the fracture side and allowing the moving wall to close on the proppant.

Figure 10:
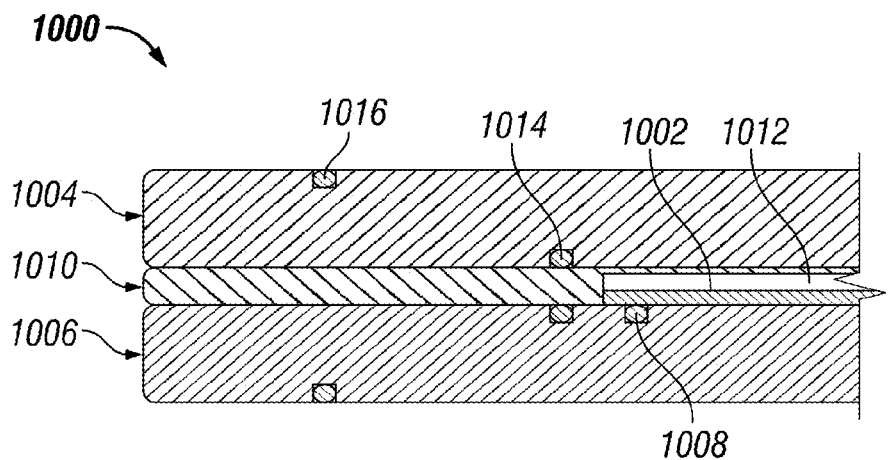
FIG. 10 depicts in cross-sectional view, an embodiment including a porous plate disposed in test cell fluid flow gap, in accordance with the disclosure.

In some other embodiments of the disclosure, a porous plate is disposed within the fluid flow gap of the test cell. In such embodiments, light passes through the porous plate, and test fluid passes through as well by controlled leak off. FIG. 10 depicts such an arrangement in a cross-sectional view. A portion of test cell 1000 is shown which includes porous plate 1002, which may be a sintered polyethylene sheet that allows controlled leak off for example, disposed between first textured wetted plate 1004 and second textured wetted plate 1006. In some cases, porous plate 1002 is made of light transmitting material. Porous plate 1002 has separate leak off zones (six shown) providing localized leak off study, and/or providing uniform control by pumping out of each zone with an equal rate. The O-ring 1008 seals off one of the zones. Spacer 1010 sets width of the test cell fluid flow gap 1012, partially filled with porous plate 1002. The two O-rings 1014 seal the test fluid in the test cell, and O-rings 1016 are used to vacuum clamp the texture plates against the structural support system. In some further aspects, a test cell system that allows controlled cross flow includes a plurality of porous plates, such as four or more, which are inserted on each edge. Such a design will allow test fluid passage without sand or proppant flow. In another aspect, a large area porous plate may advantageously combined with the moving wall system detailed above to accurately simulate fluid leaking off into a porous formation during fracture closure.

Figure 11A:
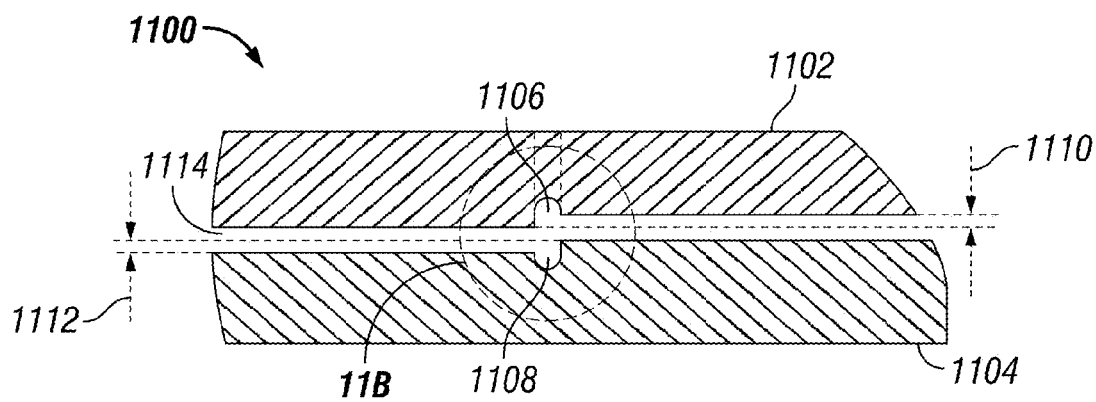
FIG. 11 shows in cross-sectional view, an embodiment of a variable width test cell fluid flow gap using steps formed in the textured wetted plates, according to the disclosure; and, FIG. 12 illustrates in a face view, an embodiment of a textured wetted plate having fluid ports and thermocouple wells formed therein, in accordance with the disclosure.
Figure 11B:
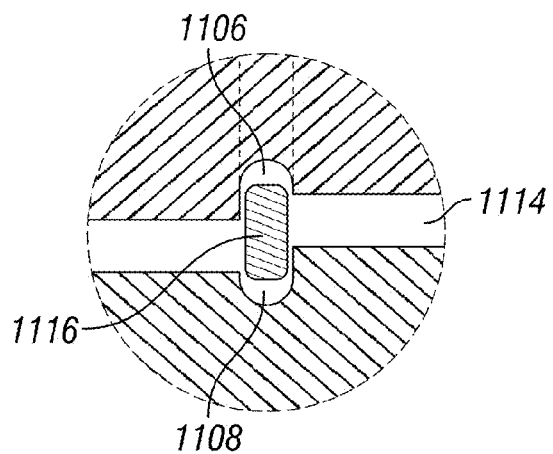

In some aspects, textured plates may be used which include adjustable steps that when sliding the plates relative to one another, the width of the test cell fluid flow gap at the step can be adjusted. FIG. 11 depicts such an arrangement in a cross-sectional view. In FIG. 11, a portion of first textured wetted plate 1102 and second textured wetted plate 1104 are shown. Step areas 1106 and 1108 are formed into first textured wetted plate 1102 and second textured wetted plate 1104, respectively. Further, each textured wetted plate 1102 and 1104 is milled with different thicknesses having offset 1110 and 1112. In some aspects, the step areas 1106 and 1108 shown may be useful to simulate crossing a natural fracture, when the test fluid passes through the pockets formed by step areas 1106 and 1108 in the crossing area. Further, by sliding textured wetted plates 1102 and 1104 relative one another the width of the gap formed at step areas 1106 and 1108 can be adjusted. A spacer plate (not shown) disposed around the periphery of the cell adjusts/fixes the width of the flow gap. Shim(s) 1116 may be disposed in the ends of the areas 1106 and 1108 to precisely control the step area spacing, as shown in the additional cross section presented.

Figure 12:
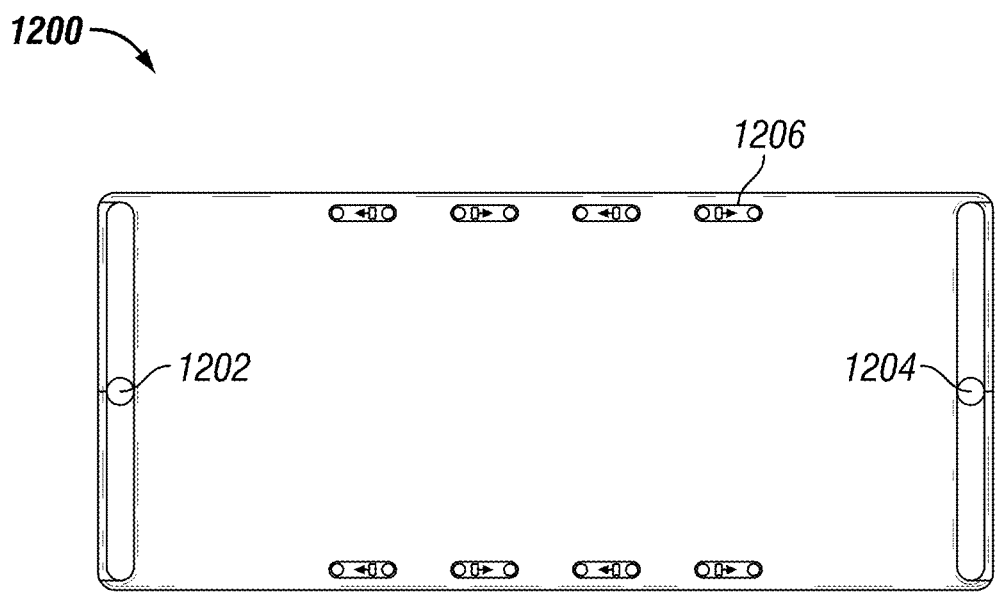

In some aspects of the disclosure, textured wetted plates that are non-structural allow considerable flexibility in the function of the surfaces. Textured wetted plate 1200 may include ports 1202 and 1204, which may be cross drilled to allow addition of chemicals or removal of samples, as illustrated in the embodiment depicted in FIG. 12 in a face view. Flow ports 1206 (eight shown) may be formed in the plate in such that they are very close to the fluid flow gap. Ports may be located further from the edges than shown and may be larger or smaller, and thermocouple ports may be readily located at any desired position. Sensors or electrical connections may be installed in or molded into the textured plate. Textured wetted plate with matching machined textures may also be used to simulate the book matching that is seen in rock that has been split in two. In some cases, real rock textures (or mathematical simulations of rock textures) may be machined into the face of the textured wetted plates.

Generally, apparatus according to and used in methods of the disclosure are of a design and construction sufficient to allow desired fluid injection rates, injection pressures and temperatures into the textured fluid flow gap for viewing or otherwise analyzing fluid/particle behavior and characteristics while moving through the gap. Basic components are readily known to those of skill in the art. Components may include, but are not limited to, piston/cylinder arrangements, power sources, conduits, valves, frames and fasteners, sample supply and waste means, motors, controllers, computers, spectrophotomers, x-ray sources, transducers, and the like.

The foregoing description of the embodiments has been provided for purposes of illustration and description. Example embodiments are provided so that this disclosure will be sufficiently thorough, and will convey the scope to those who are skilled in the art. Numerous specific details are set forth such as examples of specific components, devices, and methods, to provide a thorough understanding of embodiments of the disclosure, but are not intended to be exhaustive or to limit the disclosure. It will be appreciated that it is within the scope of the disclosure that individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Also, in some example embodiments, well-known processes, well-known device structures, and well-known technologies are not described in detail. Further, it will be readily apparent to those of skill in the art that in the design, manufacture, and operation of apparatus to achieve that described in the disclosure, variations in apparatus design, construction, condition, erosion of components, gaps between components may present, for example.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly. In the figures illustrated, the orientation of particular components is not limiting, and are presented and configured for an understanding of some embodiments of the disclosure.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. An apparatus comprising:
   a test cell body having a first exterior surface and a second exterior surface, and a cavity extending between the first exterior surface and the second exterior surface;
   a first textured wetted plate and a second textured wetted plate disposed within the cavity, wherein an adjustable width fluid flow gap is defined between the first textured wetted plate and the second textured wetted plate, wherein the first textured wetted plate and the second textured wetted plate have steps formed in opposing surfaces;
an illuminator disposed between the second textured wetted plate and the second exterior surface; and,
a viewing window formed within the first exterior surface, wherein the adjustable width is varied by sliding the first textured wetted plate and the second textured wetted plate.

2. The apparatus of claim 1 wherein the first textured wetted plate and the second textured wetted plate comprise opposed mated surfaces.

3. The apparatus of claim 2 wherein the first textured wetted plate and the second textured wetted plate comprise surfaces simulating split rock.

4. The apparatus of claim 2 wherein the first textured wetted plate and the second textured wetted plate comprise hexagonal textured surfaces.

5. The apparatus of claim 2 wherein the first textured wetted plate and the second textured wetted plate comprise ripple textured surfaces.

6. The apparatus of claim 2 wherein the first textured wetted plate and the second textured wetted plate comprise fine grain textured surfaces.

7. The apparatus of claim 1 wherein the first textured wetted plate and the second textured wetted plate are transparent.

8. The apparatus of claim 7 wherein the first textured wetted plate and the second textured wetted plate comprise opposed mated surfaces.

9. The apparatus of claim 1 wherein the first textured wetted plate and the second textured wetted plate have multiple dimensional scale texture patterns, wherein the texture patterns are defined by a micrometer scale, a 1 mm to 5 mm scale, and a 10 mm to 200 mm scale.

10. The apparatus of claim 1 wherein the first exterior surface comprises a deflection brace disposed within the viewing window and adjacent the first textured wetted plate.

11. The apparatus of claim 1 wherein a plurality of spacers is disposed between the first textured wetted plate and the second textured wetted plate, and adjacent the fluid flow gap to define a fluid flow gap width.

12. The apparatus of claim 1 wherein the adjustable width is varied by deflection of the first textured wetted plate.

13. The apparatus of claim 1 wherein a portion of the fluid flow gap comprises a porous plate disposed therein.

14. The apparatus of claim 1 further comprising transparent means for heating and controlling the temperature of the fluid flow gap, wherein the transparent means for heating and controlling are disposed between the first textured wetted plate and the body, and disposed between the second textured wetted plate and the body.

15. The apparatus of claim 1 further comprising means for heating and controlling the temperature of the fluid flow gap which are disposed within or adjacent the body.

16. A system comprising:
a test cell having an adjustable width fluid flow gap defined between a first textured wetted plate and a second textured wetted plate, wherein the plates are transparent and the plates have steps formed in opposing surfaces;
an illuminator disposed adjacent the second textured wetted plate;
a viewing window adjacent the first textured wetted plate;
a support surface disposed adjacent the second textured wetted plate; and,
a test fluid disposed within the fluid flow gap,
wherein the adjustable width is varied by sliding the first textured wetted plate and the second textured wetted plate.

17. The system of claim 16 wherein the test fluid is a subterranean formation treatment fluid comprising proppant.

18. The system of claim 16 wherein the first and second textured wetted plates are substantially supported from internal pressure by the viewing window and the support surface.

19. The system of claim 16 wherein the support surface is metallic.

20. The system of claim 16 wherein the adjustable width gap between the first and second textured wetted plates may be adjusted while the fluid flow gap is pressurized.

21. A system comprising:
an adjustable width test cell fluid flow gap defined between a first textured wetted plate and a second textured wetted plate, wherein the plates are transparent and the plates have steps formed in opposing surfaces;
a plurality of spacers disposed between the first textured wetted plate and the second textured wetted plate, and adjacent the fluid flow gap to define a fluid flow gap width; and,
a viewing window adjacent the first textured wetted plate, wherein the adjustable width is varied by sliding the first textured wetted plate and the second textured wetted plate.

22. The system of claim 21 wherein the first textured wetted plate and the second textured wetted plate comprise opposed mated surfaces having a pattern selected from one of simulation of split rock, hexagonal texture, ripple texture, and fine grain texture.

* * * * *